(12) United States Patent
Yang et al.

(10) Patent No.: US 8,505,398 B2
(45) Date of Patent: Aug. 13, 2013

(54) DISSOLUTION PROPERTIES MEASUREMENT SYSTEM USING PIEZOELECTRIC SENSOR

(75) Inventors: Ju Hwan Yang, Gyunggi-do (KR); Jae Woo Joung, Gyunggi-do (KR); Ji Han Kwon, Gyunggi-do (KR); Young Seuck Yoo, Seoul (KR)

(73) Assignee: Samsung Electro-Mechanics Co., Ltd., Suwon (KR)

( * ) Notice: Subject to any disclaimer, the term of this patent is extended or adjusted under 35 U.S.C. 154(b) by 105 days.

(21) Appl. No.: 13/064,419

(22) Filed: Mar. 23, 2011

(65) Prior Publication Data

US 2012/0024088 A1 Feb. 2, 2012

(30) Foreign Application Priority Data

Jul. 29, 2010 (KR) .................. 10-2010-0073638

(51) Int. Cl.
*G01B 21/00* (2006.01)
(52) U.S. Cl.
USPC .......................................... 73/866; 73/150 R
(58) Field of Classification Search
None
See application file for complete search history.

(56) References Cited

U.S. PATENT DOCUMENTS

| 4,098,662 A * | 7/1978 | Schell et al. ................... 204/404 |
| 4,108,602 A * | 8/1978 | Hanson et al. ................... 436/52 |
| 4,593,563 A * | 6/1986 | Laine et al. ................... 73/865.8 |
| 5,076,107 A * | 12/1991 | Timmermans et al. ......... 73/866 |
| 2006/0037416 A1 * | 2/2006 | Roth ............................... 73/866 |

FOREIGN PATENT DOCUMENTS

| JP | 7-12702 | 1/1995 |
| JP | 2003-503731 | 1/2003 |
| JP | 2005-284143 | 10/2005 |
| JP | 2008-89348 | 4/2008 |
| KR | 10-2006-0080391 | 7/2006 |
| WO | WO 01/02834 A1 | 11/2001 |

OTHER PUBLICATIONS

Japanese Office Action for corresponding Japanese application No. 2011-070827 issued Oct. 16, 2012.

* cited by examiner

*Primary Examiner* — Robert R Raevis

(57) ABSTRACT

There is provided a dissolution properties measurement system using a piezoelectric sensor, capable of continuously measuring dissolution properties of a substrate in an aqueous solution by using the piezoelectric sensor. The dissolution properties measurement system includes: a specimen receiving unit including a chamber receiving a specimen therein; a mass measuring unit connected with the specimen to measure a mass change of the specimen in real time; and a dissolution properties measuring unit measuring a dissolution properties of the specimen on the basis of the value measured by the mass measuring unit.

14 Claims, 4 Drawing Sheets

DISSOLUTION PROPERTIES MEASUREMENT SYSTEM USING PIEZOELECTRIC SENSOR

CROSS-REFERENCE TO RELATED APPLICATIONS

This application claims the priority of Korean Patent Application No. 10-2010-0073638 filed on Jul. 29, 2010, in the Korean Intellectual Property Office, the disclosure of which is incorporated herein by reference.

BACKGROUND OF THE INVENTION

1. Field of the Invention

The present invention relates to a system of measuring dissolution properties of an ink pattern printed on a substrate, and more particularly, to a dissolution properties measurement system using a piezoelectric sensor, which is capable of continuously measuring dissolution properties of a substrate in an aqueous solution by using the piezoelectric sensor.

2. Description of the Related Art

In general, ink is printed on a PCB substrate and a package (PKG) including the same, according to various purposes. For example, the printing of ink may be used for marking or the prevention of gold plating.

As an ink pattern printed on aboard is subjected to a post processing such as plating, the dissolution thereof is generated by various surrounding environments. Such a change in mass is minute; however as a result, it serves as an index of printing quality and durability after printing.

Accordingly, a system capable of easily detecting and measuring changes in dissolution is required.

SUMMARY OF THE INVENTION

An aspect of the present invention provides a dissolution properties measurement system capable of easily detecting and measuring changes of dissolution in an ink pattern printed on a board.

According to an aspect of the present invention, there is provided dissolution properties measurement system including: a specimen receiving unit including a chamber receiving a specimen therein; a mass measuring unit connected with the specimen to measure a mass change of the specimen in real time; and a dissolution properties measuring unit measuring a dissolution properties of the specimen on the basis of the value measured by the mass measuring unit.

The system may further include a mass change transferring unit transferring force corresponding to the mass change of the specimen to the mass measuring unit.

The specimen receiving unit may include a solution filled in the chamber and in which the specimen is immersed.

The system may further include a specimen supporting unit supporting the specimen in the chamber.

The specimen supporting unit may be made of a material having acid resistance and corrosion resistance.

The chamber and the specimen supporting unit may be made of glass or Teflon.

The mass measuring unit may include: a weight connected with the specimen; and a mass measuring sensor supporting the weight and measuring a mass change of the weight.

The weight may be made of a metallic material and an antioxidation layer is formed on the surface of the weight.

The mass measuring sensor may be a piezoelectric sensor.

The dissolution properties measuring unit may include: a signal amplifying portion amplifying a mass change signal transmitted from the mass measuring unit; a signal converting portion receiving the signal amplified from the signal amplifying portion and converting the received signal into a digital signal; and an analysis portion receiving the digital signal and analyzing the dissolution properties on the basis of the received digital signal.

The dissolution properties measuring unit may further include a graph display portion displaying the mass change of the specimen through a graph in real time.

The mass change transferring unit may include: a connection wire connecting the specimen supporting unit and the mass measuring unit; and at least one pulley unit supporting the connection wire.

The connection wire may be made of a metallic material having acid resistance and corrosion resistance.

The connection wire may be made of stainless steel.

The mass change transferring unit may include: a pulley unit of which one end is connected with the mass measuring unit; and a connection wire connecting the other end of the pulley unit and the specimen supporting unit.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
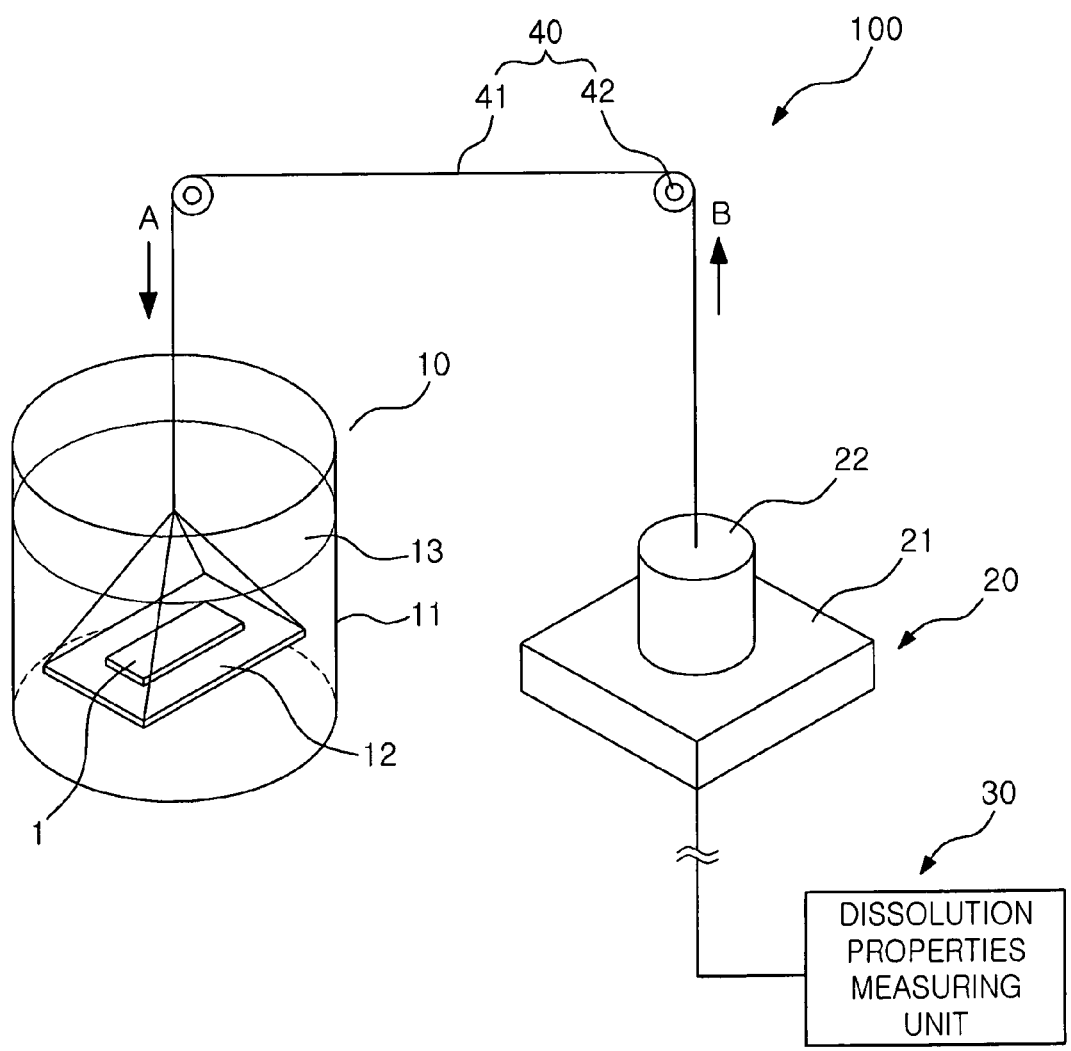
FIG. 1 is a diagram schematically showing a dissolution properties measurement system according to an exemplary embodiment of the present invention.

Prior to the detailed description of the present invention, terms or words used in the specification and the appended claims should not be construed as having normal or dictionaric meanings, and should be construed as having meanings and concepts which conform with the spirit of the present invention according to a principle that the inventor can properly define the concepts of the terms in order to describe his/her own invention in the best way. Accordingly, embodiments disclosed in the specification and configurations shown in the accompanying drawings are just the most preferred embodiments, but are not limited to the spirit and scope of the present invention. Therefore, at the time of this application, it will be appreciated that various equivalents and modifications may be included within the spirit and scope of the present invention.

Hereinafter, exemplary embodiments of the present invention will be described in detail with reference to the accompanying drawings. In this case, like reference numerals refer to like elements in the accompanying drawings. Further, a detailed description of known functions and components which may obscure the spirit of the present invention will be omitted. For the same reason, some components are exaggerated or omitted or schematically shown in the accompanying drawings and the size of each component does not fully reflect the actual size thereof.

Hereinafter, exemplary embodiments of the present invention will be described in detail with reference to the accompanying drawings.

Figure 2:
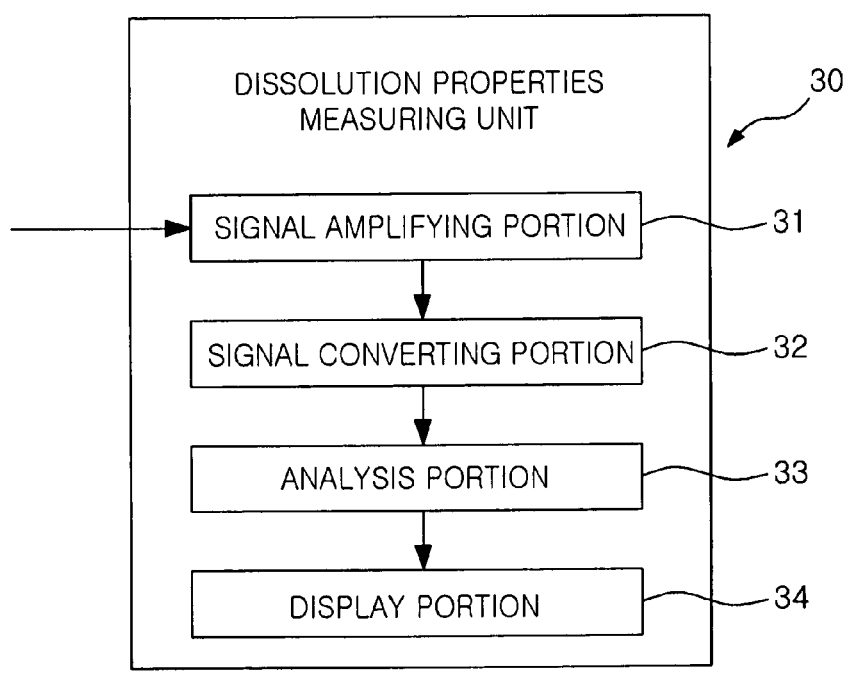
FIG. 2 is a schematic block diagram of a dissolution properties measurement unit shown in FIG. 1.

FIG. 1 is a diagram schematically showing a dissolution properties measurement system according to an exemplary embodiment of the present invention and FIG. 2 is a schematic block diagram of a dissolution properties measurement unit shown in FIG. 1.

Referring to FIGS. 1 and 2, the dissolution properties measurement system 100 according to the exemplary embodiment of the present invention may include a specimen receiving unit 10, a mass measuring unit 20, a mass change transferring unit 40, and a dissolution properties measurement unit 30.

The specimen receiving unit 10 includes a chamber 11 receiving a specimen 1 therein and a specimen supporting unit 12 supporting the specimen 1 inside the chamber 11.

In the exemplary embodiment, measuring dissolution properties of the ink printed on a board will be described as an example. Accordingly, as specimen 1 according to the exemplary embodiment, a board of which at least one surface is printed with an ink pattern is employed. However, the present invention is not limited thereto.

The chamber 11 may be formed as a vessel and may be filled with a solution 13 in which the specimen 1 is immerged. In this case, as the solution 13 filled in the chamber 11, various kinds of solution 13 may be used to correspond to the specimen 1 to be measured and for example, an acid solution or distilled water may be used.

As described above, since the chamber 11 may be filled with the acid solution 13, the chamber 11 is preferably made of a material having acid resistance and corrosion resistance and for example, it may be made of glass or Teflon. However, the material of the chamber 11 is not limited thereto.

The specimen supporting unit 12 supports the specimen 1 inside the chamber 11. The specimen supporting unit 12 is formed as a plate, the specimen 1 is seated on the top surface thereof and a connection wire 41 is connected thereto through the side or edge thereof. The specimen supporting unit 12 may maintain a floating state in which it floats in the inner space of the chamber 11 without contacting the bottom surface of the chamber 11 and this state may be implemented by the tension of the connection wire 41 supporting the specimen supporting unit 12 upwardly.

Similarly to the chamber 11, the specimen supporting unit 12 may support the specimen 1 while the specimen 1 is immersed in the acid solution 13 as necessary. Accordingly, the specimen supporting unit 12 may be preferably made of the material having acid resistance and corrosion resistance, and, for example, it may be made of glass or Teflon. However, the material of the specimen supporting unit 12 is not limited thereto.

The mass measuring unit 20 is connected with the specimen 1 to measure a mass change of the specimen 1 in real time and is configured to include a weight 22 and a mass measuring sensor 21.

The weight 22 is directly connected with the specimen 1 through the connection wire 41 to be described below and receives corresponding force depending on the mass change of the specimen 1. Therefore, the weight 22 may be heavier than the specimen 1 and may be made of a metallic material. Further, an antioxidation layer for preventing the weight 22 from being oxidized by a surrounding environment may be formed on the surface of the weight 22.

The mass measuring sensor 21 supports the weight at the lower part of the weight 22 and measures the mass change of the weight 22.

The dissolution properties measurement system 100 according to the exemplary embodiment measures the mass change of the specimen 1 depending on the dissolution of ink in order to measure a dissolution degree of the ink printed on the specimen 1 which is dissolved in the solution 13 and analyzes the dissolution properties on the basis of the measurement result. Accordingly, the mass measuring sensor 21 needs to be able to easily detect the mass change of the specimen 1 due to dissolution of the ink printed on the specimen 1 and measure the amount of change.

For this, the mass measuring sensor 21 according to the exemplary embodiment may use a pressure sensor, in more detail, a piezoelectric pressure sensor (hereinafter, referred to as a piezoelectric sensor).

Certain crystals have a property, in which a voltage is induced therein, when force is received in a specific direction. A phenomenon in which the voltage is induced as above is referred to as a piezoelectric effect. The piezoelectric sensor uses the piezoelectric effect and the piezoelectric sensor according to the exemplary embodiment generates a corresponding voltage by sensitively reacting to a pressure (i.e., the mass change of the weight) applied from the outside.

The mass change transferring unit 40 may transfer the force corresponding to the mass change of the specimen 1 to the mass measuring unit 20, i.e., the weight 22 and include a connection wire 41 and a pulley unit 42.

The connection wire 41 directly connects the weight 22 of the mass measuring unit 20 with the specimen supporting unit 12, to directly transfer the mass change of the specimen 1 seated on the specimen supporting unit 12 to the weight 22. Therefore, the connection wire 41 is configured to maintain the entire part thereof in a taut state, and this state may be implemented by gravity acting on the specimen supporting unit 12.

Since one end of the connection wire 41 is fastened to the specimen supporting unit 12, the connection wire 41 is immersed in the solution 13 within the chamber 11, together with the specimen supporting unit 12. Accordingly, the connection wire 41 may be preferably made of a metallic material having acid resistance and corrosion resistance, in more detail, it may be made of stainless steel. However, the material of the connection wire 41 is not limited thereto.

The pulley unit 42 may support the connection wire 41 to easily move the connection wire 41. In the exemplary embodiment, a case of using two pulley units 42 is described as an example for convenience of description, but the number of pulley units is not limited thereto and various numbers of pulley units may be used.

According to the configuration using the pulley unit 42 and the connection wire 41, the force of gravity may act on the specimen supporting unit 12 in a downward direction, while a corresponding upward force maybe exerted on the weight 22. Therefore during the measuring the dissolution properties, since upward force may be exerted on the weight 22 in corresponding to the mass of the specimen 1, the mass of the weight 22 measured by the mass measuring sensor 21 is measured as a mass acquired by subtracting the mass of the specimen 1 from the actual mass of the weight 22.

The dissolution properties measuring unit 30 may measure the dissolution properties of the specimen 1 on the basis of the value measured by the mass measuring unit 20 and be configured to include a signal amplifying portion 31, a signal converting portion 32, an analysis portion 33, and a display portion 34.

The signal amplifying portion 31 receives and amplifies a change in voltage transmitted from the mass measuring unit 20, i.e., amass change signal. In general, since the magnitude of a signal (alternatively, voltage) outputted from the piezoelectric sensor is very small, the signal needs to be amplified. Accordingly, the signal amplifying portion 31 amplifies the signal outputted from the piezoelectric sensor in real time and thereafter, transmits the amplified signal to the signal converting portion 32.

The signal converting portion 32 receives the signal amplified from the signal amplifying portion 31 and converts the amplified signal into a digital signal. The signal transmitted from the signal converting unit 32 is an analog signal generated according to changes in voltage. Accordingly, the signal converting portion 32 converts the analog signal into the digital signal so as to easily record and use the analog signal as data.

The analysis portion 33 receives the digital signal from the signal converting portion 32 and analyzes the dissolution properties on the basis of the received digital signal. That is, the analysis portion 33 analyzes a degree and a state of ink, in which the ink is dissolved from the specimen 1 on the basis of the mass change of the specimen 1. The analysis result may be outputted through diversified routes. For example, the analysis result may be displayed on a monitor in real time or may be continuously printed through a printer. Further, both the digital signal and the analysis result may be stored and desired data may be extracted and used as necessary afterwards.

The display portion 34 displays diversified analysis results analyzed by the analysis portion 33 to a user. For this, the display portion 34 may include the monitor, and the like. Further, the display portion 34 may display the mass change of the specimen 1 through a graph in a real time. This may be performed by the display portion 34 continuously displaying the digital signal converted by the signal converting portion 32 according to the time. However, the present invention is not limited thereto.

Next, a dissolution properties measurement method of the dissolution properties measurement system 10 according to the exemplary embodiment will be described.

In the dissolution properties measurement method according to the exemplary embodiment of the present invention, a specimen 1, of which dissolution properties are to be measured is seated on the specimen supporting unit 12 and thereafter, the specimen supporting unit 12 is immersed in the chamber 11 in operation S10.

In this case, force equal to the mass of the specimen 1 acts in direction A on the specimen supporting unit 12, and as a result, force equal to the mass of the specimen 1 acts on the weight 22 upwardly, i.e., force acts in direction B in an amount equal to the mass of the specimen supporting unit 12 of the specimen 1 by the connection wire 41 connected with the specimen supporting unit 12. Accordingly, as described above, as the mass of the weight 22 measured by the mass measuring sensor 21, the mass acquired by subtracting the mass of the specimen 1 from the actual mass of the weight 22 is measured.

In this case, the masses of the specimen 1 and the specimen supporting unit 12 are much smaller than the mass of the weight 22. Accordingly, even though upward force may be exerted on the weight 22, the weight does not fully float from the mass measuring sensor 21 and only a slight change in mass is generated.

Subsequently, in operation S2, ink is dissolved from the specimen 1 positioned in the chamber 11. When the ink is dissolved from the specimen 1, the mass of the specimen 1 is decreased by as much as the dissolved ink. As the mass of the specimen 1 is decreased, the upward force exerted on the weight 22, may also be decreased to correspond to the decrease amount of the mass of the specimen 1.

As a result, the mass of the weight 22 is increased, corresponding to the decrease in the amount of mass of the specimen 1. The mass change of the weight 22 is sensed by the mass measuring sensor 21 and a corresponding voltage thereof is outputted in real time.

The change in the voltage outputted from the mass measuring sensor 21 in real time is transmitted to the dissolution properties measuring unit 30 and amplified and converted by the signal amplifying portion and the signal converting portion, respectively, and thereafter, analyzed by the analysis portion. In addition, the finally analyzed data is displayed to the user through the display portion 34, and the like.

Figure 3A:
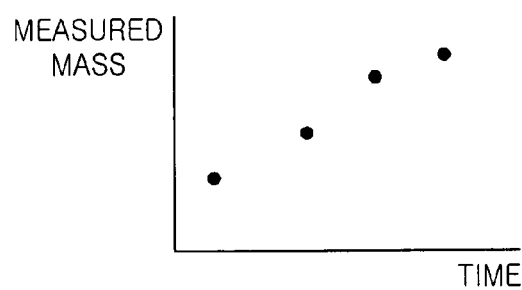
FIG. 3A is a diagram schematically showing a measurement graph of a dissolution properties measurement system according to the related art.
Figure 3B:
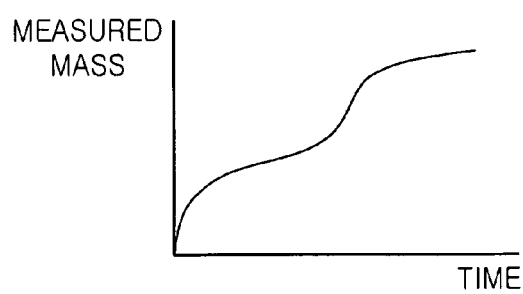
FIG. 3B is a diagram schematically showing a measurement graph of a dissolution properties measurement system according to an exemplary embodiment of the present invention.

FIG. 3A is a diagram schematically showing a measurement graph of a dissolution properties measurement system according to the related art and FIG. 3B is a diagram schematically showing a measurement graph of a dissolution properties measurement system according to an exemplary embodiment of the present invention.

In the related art, a method of examining dissolution properties by periodically testing the specimen or the solution in which the specimen is immersed, according to a predetermined time interval is used. Therefore, as shown in FIG. 3A, the measurement graph is discontinuously illustrated and individual measurement values are measured at periodic examination points of time.

However, in the dissolution properties measurement system according to the present invention, the specimen 1 is continuously immersed in the chamber 11, and as a result, as shown in FIG. 3B, the dissolution properties measurement graph is measured in real time and displayed continuously. Accordingly, the change of the dissolution properties according to the total measurement time may be verified and a specific reaction time when an inflection point is generated according to the time may be detected. As a result, it is possible to determine a dissolution mechanism.

The present invention is not limited to the exemplary embodiment and is variously applicable.

Figure 4:
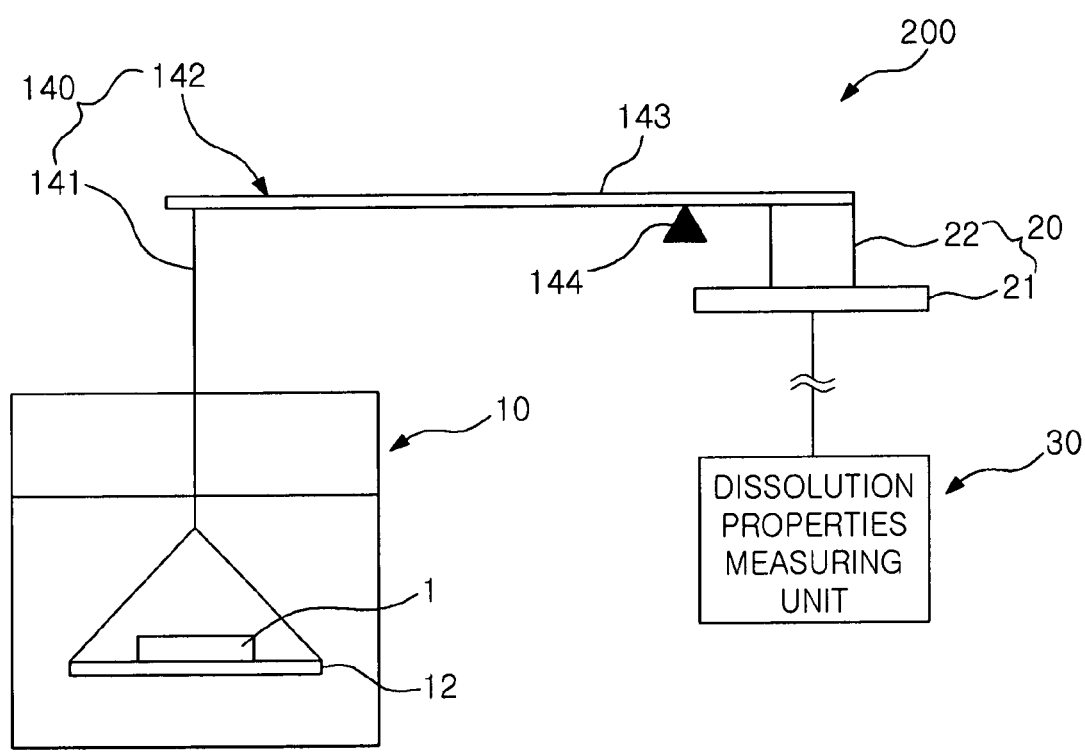
FIG. 4 is a diagram showing a dissolution properties measurement system according to another exemplary embodiment of the present invention.

FIG. 4 is a diagram showing a dissolution properties measurement system according to another exemplary embodiment of the present invention. Referring to FIG. 4, the dissolution properties measurement system 200 according to the exemplary embodiment is configured similarly as that of the above-mentioned exemplary except for the configuration of a mass change transferring unit 140. Accordingly, the same components as in the above-mentioned exemplary embodiment will not be described and only the mass change transferring unit 140 will be primarily described.

The mass change transferring unit 140 according to the exemplary embodiment includes a connection wire 141 and a lever unit 142.

The lever unit 142 includes a lever 143 and a stand 144 for implementing a principle of the lever and one end of the lever 143 is connected with the weight 22 of the mass measuring unit 20. In more detail, one end of the lever 143 is fastened to the top surface of the weight 22 to be integrated with the weight 22.

Further, the connection wire 141 connects the other end of the lever 143 and the specimen supporting unit 12 to each other. In this case, the connection wire 141 connects the specimen supporting unit 12 and the other end of the lever 143 to each other so that the force of gravity may act on the specimen supporting unit 12 in a downward direction. Accordingly, force is applied downwardly to even the other end of the lever 143.

Further, since the other end of the lever 143 receives force downwardly by the specimen supporting unit 12, one end of the lever 143 which is fastened to the weight 22 receives force upwardly. Therefore, since force acts on the weight 22 in the same direction as the above-mentioned exemplary embodiment, the dissolution properties may be measured through the same process as the above-mentioned exemplary embodiment.

As described above, in the dissolution properties measurement system 200 according to the exemplary embodiment using the lever unit 142, when the stand 144 is disposed adjacent to the weight 22, force generated by a minute mass change of the specimen 1 is amplified and applied to the weight 22 of the mass measuring sensor 21. Accordingly, it is possible to more easily sense the mass change of the specimen 1.

In the dissolution properties measurement system according to the present invention configured as above, since the mass change of the specimen is sensed and analyzed in real time, dissolution properties analysis data is measured in real time and displayed continuously.

Accordingly, it is possible to detect a specific reaction time when an inflection point is generated according to the time, and based on this, it is possible to determine a dissolution mechanism.

Further, since the minute mass change can be sensed by using the piezoelectric sensor, more precise measurement data can be acquired. Moreover, since the specimen is continuously positioned in the chamber throughout the measurement process, it is possible to minimize mistakes or errors generated as the specimen is inputted into various processes.

As set forth above, according to the exemplary embodiments of the present invention, since the dissolution properties measurement system detects and analyzes a mass change of a specimen in real time, dissolution properties analysis data is measured in real time and continuously displayed.

Therefore, it is possible to detect a specific reaction time when an inflection point is generated according to the time and, based on this, it is possible to determine a dissolution mechanism.

Further, since it is possible to sense even a minute mass change by using a piezoelectric sensor, more precise measurement data can be acquired.

Moreover, in the present invention, since a specimen is continuously positioned in a chamber throughout a measurement process, it is possible to minimize mistakes or errors which are generated as the specimen is inputted into multiple processes as in the related art.

Meanwhile, the dissolution properties measurement system according to the present invention is not limited to the above-mentioned exemplary embodiments and various modifications can be made by those skilled in the art without departing from the spirit of the present invention.

Further, although the case of measuring the dissolution properties of ink printed on the board has been described as an example in the exemplary embodiment, the dissolution properties measuring target is not limited to the board or ink and diversified specimens may be used in order to measure dissolution properties of diversified materials in addition to ink.

While the present invention has been shown and described in connection with the exemplary embodiments, it will be apparent to those skilled in the art that modifications and variations can be made without departing from the spirit and scope of the invention as defined by the appended claims. Accordingly, the scope of the present invention will be determined by the appended claims.

What is claimed is:

1. A dissolution measurement system, comprising:
 a specimen receiving unit including a chamber receiving a specimen therein;
 a mass measuring unit connected with the specimen to measure a mass change of the specimen in real time; and
 a dissolution measuring unit measuring dissolution degree of the specimen on the basis of the value measured by the mass measuring unit,
 the mass measuring unit including a mass measuring sensor and a weight connected to the specimen and applying pressure to the mass measuring sensor, wherein the mass measuring sensor measures a change of the pressure by dissolution of the specimen.

2. The system of claim 1, further comprising: a mass change transferring unit transferring force corresponding to the mass change of the specimen to the mass measuring unit.

3. The system of claim 2, further comprising: a specimen supporting unit supporting the specimen in the chamber.

4. The system of claim 3, wherein the specimen supporting unit is made of a material having acid resistance and corrosion resistance.

5. The system of claim 3, wherein the chamber and the specimen supporting unit are made of glass or Teflon.

6. The system of claim 1, wherein the specimen receiving unit includes a solution filled in the chamber and in which the specimen is immersed.

7. The system of claim 1, wherein the weight is made of a metallic material and an antioxidation layer is formed on the surface of the weight.

8. The system of claim 1, wherein the mass measuring sensor is a piezoelectric sensor.

9. The system of claim 1, wherein the dissolution measuring unit includes:
 a signal amplifying portion amplifying a mass change signal transmitted from the mass measuring unit;
 a signal converting portion receiving the signal amplified from the signal amplifying portion and converting the received signal into a digital signal; and
 an analysis portion receiving the digital signal and analyzing the dissolution degree on the basis of the received digital signal.

10. The system of claim 9, wherein the dissolution measuring unit further includes a graph display portion displaying the mass change of the specimen through a graph in real time.

11. A dissolution measurement system, comprising:
 a specimen receiving unit including a chamber receiving a specimen therein;
 a mass measuring unit connected with the specimen to measure a mass change of the specimen in real time;
 a dissolution measuring unit measuring dissolution degree of the specimen on the basis of the value measured by the mass measuring unit;
 a specimen supporting unit supporting the specimen in the chamber; and
 a mass change transferring unit transferring force corresponding to the mass change of the specimen to the mass measuring unit, the mass change transferring unit including
 a connection wire connecting the specimen supporting unit and the mass measuring unit, and
 at least one pulley unit supporting the connection wire.

12. The system of claim 11, wherein the connection wire is made of a metallic material having acid resistance and corrosion resistance.

13. The system of claim 11, wherein the connection wire is made of stainless steel.

14. A dissolution measurement system, comprising:
- a specimen receiving unit including a chamber receiving a specimen therein;
- a mass measuring unit connected with the specimen to measure a mass change of the specimen in real time;
- a dissolution measuring unit measuring dissolution degree of the specimen on the basis of the value measured by the mass measuring unit;
- a specimen supporting unit supporting the specimen in the chamber; and
- a mass change transferring unit transferring force corresponding to the mass change of the specimen to the mass measuring unit, the mass change transferring unit including
  - a lever unit of which one end is connected with the mass measuring unit, and
  - a connection wire connecting the other end of the lever unit and the specimen supporting unit.

* * * * *